US009174896B2

(12) United States Patent
Nappa et al.

(10) Patent No.: US 9,174,896 B2
(45) Date of Patent: Nov. 3, 2015

(54) CATALYTICAL SYNTHESIS OF INTERNAL FLUOROBUTENES AND INTERNAL FLUOROPENTENES

(75) Inventors: Mario Joseph Nappa, Newark, DE (US); Ekaterina N Swearingen, Wilmington, DE (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 80 days.

(21) Appl. No.: 13/988,111

(22) PCT Filed: Nov. 7, 2011

(86) PCT No.: PCT/US2011/059497
§ 371 (c)(1),
(2), (4) Date: Jun. 13, 2013

(87) PCT Pub. No.: WO2012/067864
PCT Pub. Date: May 24, 2012

(65) Prior Publication Data
US 2014/0114096 A1 Apr. 24, 2014

(30) Foreign Application Priority Data
Nov. 17, 2010 (RU) ................................ 2010147004

(51) Int. Cl.
C07C 17/25 (2006.01)
C07C 17/20 (2006.01)
C07C 21/18 (2006.01)

(52) U.S. Cl.
CPC .............. *C07C 17/25* (2013.01); *C07C 17/206* (2013.01)

(58) Field of Classification Search
CPC .......... C07C 17/25; C07C 21/18; C07C 17/20
USPC ................... 570/156, 155, 160, 161
See application file for complete search history.

(56) References Cited

U.S. PATENT DOCUMENTS

| 2,271,356 A | 1/1942 | Turkevich et al. |
| 3,258,500 A | 6/1966 | Swamer et al. |
| 4,828,818 A | 5/1989 | Carlson et al. |
| 5,036,036 A | 7/1991 | Lerou |
| 6,031,141 A | 2/2000 | Mallikarjuna et al. |
| 2006/0106263 A1* | 5/2006 | Miller et al. ............... 570/155 |
| 2010/0210882 A1* | 8/2010 | Sharratt et al. ............ 570/142 |

FOREIGN PATENT DOCUMENTS

| WO | 2008040969 A2 | 4/2008 |
| WO | 2010055146 A2 | 5/2010 |
| WO | WO 2010055146 A2 * | 5/2010 |
| WO | 2012067865 A1 | 5/2012 |
| WO | 2012067870 A1 | 5/2012 |
| WO | 2012067872 A1 | 5/2012 |

OTHER PUBLICATIONS

Ruthruff, "Inorganic Synthesis", vol. II, pp. 190-193, 1946 by McGraw-Hill Book Co., New York.
International Search Report, PCT/US2011/059497, Filing Date Nov. 7, 2011, Mailed on Feb. 1, 2012.

* cited by examiner

*Primary Examiner* — Fereydoun G Sajjadi
*Assistant Examiner* — Medhanit Bahta

(57) ABSTRACT

A vapor phase process is disclosed for making internal fluorobutenes. The process involves contacting a halobutane starting material selected from the group consisting of $CF_2HCHClCH_2CCl_2H$, $CF_2HCHClCH_2CCl_3$, $CF_3CHClCH_2CCl_2H$, $CF_3CHClCH_2CCl_3$, $CF_3CHClCHClCCl_2H$, $CF_3CHClCHClCCl_3$, $CF_3CCl_2CH_2CCl_2H$, $CF_3CCl_2CH_2CCl_3$, $CF_3CCl_2CHClCCl_2H$, $CF_3CCl_2CHClCCl_3$, $CF_3CClFCHClCCl_2H$, $CF_3CClFCHClCCl_3$, $CF_3CClFCH_2CCl_2H$, $CF_3CClFCH_2CCl_3$, $CF_3CClFCHFCCl_2H$, $CF_3CClFCHFCCl_3$, $CF_3CClHCHFCCl_2H$ and $CF_3CClHCHFCCl_3$, with HF in a reaction zone in the presence of a chromium oxyfluoride catalyst to produce a product mixture comprising an internal fluorobutene. Another vapor phase process is disclosed for making internal fluoropentenes. The process involves contacting a halopentane starting material selected from the group consisting of $CF_2HCHXCH_2CX_2CX_3$, $CF_3CHXCH_2CX_2CX_3$, $CF_3CHXCHXCX_2CX_3$, $CF_3CX_2CH_2CX_2CX_3$, $CF_3CX_2CHXCX_2CX_3$ and $CF_3CHXCHFCX_2CX_3$, with HF in a reaction zone in the presence of a chromium oxyfluoride catalyst to produce a product mixture comprising an internal fluoropentene, wherein each X is independently selected from the group consisting of F, Cl and Br, provided that not all X are fluorines.

20 Claims, No Drawings

CATALYTICAL SYNTHESIS OF INTERNAL FLUOROBUTENES AND INTERNAL FLUOROPENTENES

This application represents a national filing under 35 U.S.C. 371 of International Application No. PCT/US11/59497 filed Nov. 7, 2011.

BACKGROUND

1. Field of the Disclosure

This disclosure relates in general to the preparation of internal fluorobutenes and internal fluoropentenes using halobutanes and halopentanes as starting materials respectively in vapor phase processes catalyzed by chromium oxyfluoride.

2. Description of Related Art

CFCs (chlorofluorocarbons) and HCFCs (hydrochlorofluorocarbons) have been employed in a wide range of applications, including their use as aerosol propellants, refrigerants, cleaning agents, expansion agents for thermoplastic and thermoset foams, heat transfer media, gaseous dielectrics, fire extinguishing and suppression agents, power cycle working fluids, polymerization media, particulate removal fluids, carrier fluids, buffing abrasive agents, and displacement drying agents. Due to the belief that CFCs and HCFCs are contributing to depletion of stratospheric ozone, there has been extensive work in the past two decades on replacement of these materials with non-ozone depleting substances. Hydrofluorocarbons (HFCs), which do not contain chlorine, have replaced CFCs and HCFCs in a number of applications. Although HFCs do not contribute to the destruction of stratospheric ozone, they are of concern due to their potential contribution to the "greenhouse effect" (global warming). Thus, there is a need for compositions in the applications noted above that do not contribute to the destruction of stratospheric ozone and also have low global warming potentials (GWPs). Certain hydrofluoroolefins, such as internal fluorobutenes and internal fluoropentenes in this disclosure, are believed to meet both goals.

BRIEF SUMMARY OF THE DISCLOSURE

The present disclosure provides a vapor phase process to make internal fluorobutenes. The process comprises contacting a halobutane starting material selected from the group consisting of $CF_2HCHClCH_2CCl_2H$, $CF_2HCHClCH_2CCl_3$, $CF_3CHClCH_2CCl_2H$, $CF_3CHClCH_2CCl_3$, $CF_3CHClCHClCCl_2H$, $CF_3CHClCHClCCl_3$, $CF_3CCl_2CH_2CCl_2H$, $CF_3CCl_2CH_2CCl_3$, $CF_3CCl_2CHClCCl_2H$, $CF_3CCl_2CHClCCl_3$, $CF_3CClFCHClCCl_2H$, $CF_3CClFCHClCCl_3$, $CF_3CClFCH_2CCl_2H$, $CF_3CClFCH_2CCl_3$, $CF_3CClFCHFCCl_2H$, $CF_3CClFCHFCCl_3$, $CF_3CClHCHFCCl_2H$ and $CF_3CClHCHFCCl_3$, with HF in a reaction zone in the presence of a chromium oxyfluoride catalyst to produce a product mixture comprising an internal fluorobutene.

The present disclosure also provides a vapor phase process to make internal fluoropentenes. The process comprises contacting a halopentane starting material selected from the group consisting of $CF_2HCHXCH_2CX_2CX_3$, $CF_3CHXCH_2CX_2CX_3$, $CF_3CHXCHXCX_2CX_3$, $CF_3CX_2CH_2CX_2CX_3$, $CF_3CX_2CHXCX_2CX_3$ and $CF_3CHXCHFCX_2CX_3$, with HF in a reaction zone in the presence of a chromium oxyfluoride catalyst to produce a product mixture comprising an internal fluoropentene, wherein each X is independently selected from the group consisting of F, Cl and Br, provided that not all X are fluorines.

DETAILED DESCRIPTION

The foregoing general description and the following detailed description are exemplary and explanatory only and are not restrictive of the invention, as defined in the appended claims. Other features and benefits of any one or more of the embodiments will be apparent from the following detailed description, and from the claims.

Disclosed is a vapor phase process for making internal fluorobutenes comprising contacting a halobutane starting material selected from the group consisting of $CF_2HCHClCH_2CCl_2H$, $CF_2HCHClCH_2CCl_3$, $CF_3CHClCH_2CCl_2H$, $CF_3CHClCH_2CCl_3$, $CF_3CHClCHClCCl_2H$, $CF_3CHClCHClCCl_3$, $CF_3CCl_2CH_2CCl_2H$, $CF_3CCl_2CH_2CCl_3$, $CF_3CCl_2CHClCCl_2H$, $CF_3CCl_2CHClCCl_3$, $CF_3CClFCHClCCl_2H$, $CF_3CClFCHClCCl_3$, $CF_3CClFCH_2CCl_2H$, $CF_3CClFCH_2CCl_3$, $CF_3CClFCHFCCl_2H$, $CF_3CClFCHFCCl_3$, $CF_3CClHCHFCCl_2H$ and $CF_3CClHCHFCCl_3$, with HF in a reaction zone in the presence of a chromium oxyfluoride catalyst to produce a product mixture comprising an internal fluorobutene.

Also disclosed is a vapor phase process for making internal fluoropentenes comprising contacting a halopentane starting material selected from the group consisting of $CF_2HCHXCH_2CX_2CX_3$, $CF_3CHXCH_2CX_2CX_3$, $CF_3CHXCHXCX_2CX_3$, $CF_3CX_2CH_2CX_2CX_3$, $CF_3CX_2CHXCX_2CX_3$ and $CF_3CHXCHFCX_2CX_3$, with HF in a reaction zone in the presence of a chromium oxyfluoride catalyst to produce a product mixture comprising an internal fluoropentene, wherein each X is independently selected from the group consisting of F, Cl and Br, provided that not all X are fluorines.

The term "internal fluorobutene" is intended to mean a partially or fully fluorinated butene wherein the carbon-carbon double bond is not at the terminal position. Examples of internal fluorobutenes in this disclosure include $CF_2HCH=CHCF_2H$, $CF_2HCH=CHCF_3$, $CF_3CH=CHCF_3$, $CF_3CF=CHCF_2H$, $CF_3CH=CFCF_2H$, $CF_3CF=CHCF_3$, $CF_3CF=CFCF_2H$ and $CF_3CF=CFCF_3$.

The term "internal fluoropentene" is intended to mean a partially or fully fluorinated pentene wherein the carbon-carbon double bond is not at the terminal position. Examples of internal fluoropentenes in this disclosure include $CF_2HCH=CHCF_2CF_3$, $CF_3CH=CHCF_2CF_3$, $CF_3CH=CFCF_2CF_3$, $CF_3CF=CHCF_2CF_3$ and $CF_3CF=CFCF_2CF_3$.

The internal fluorobutenes and internal fluoropentenes of this disclosure exist as different configurational isomers or stereoisomers. When the specific isomer is not designated, the present disclosure is intended to include all single configurational isomers, single stereoisomers, or any combination thereof. For instance, $CF_3CH=CHCF_3$ is meant to represent the E-isomer, Z-isomer, or any combination or mixture of both isomers in any ratio. Another example is $CF_3CH=CHCF_2CF_3$, by which is represented the E-isomer, Z-isomer, or any combination or mixture of both isomers in any ratio.

Although both E- and Z-isomers may be produced in the processes of this disclosure, it was found through experiments that at reaction conditions of this disclosure $CF_2HCH=CHCF_2H$, $CF_2HCH=CHCF_3$, $CF_3CH=CHCF_3$, $CF_3CF=CFCF_2H$, $CF_3CF=CFCF_3$, $CF_2HCH=CHCF_2CF_3$, $CF_3CH=CHCF_2CF_3$ or $CF_3CF=CFCF_2CF_3$ was produced with 90 mole % or more of the E-isomer while $CF_3CH=CFCF_2F_3$, $CF_3CF=CHCF_2CF_3$, $CF_3CF=CHCF_2H$, $CF_3CH=CFCF_2H$ or $CF_3CF=CHCF_3$ was produced with 90 mole % or more of the Z-isomer.

The term "halobutane" is intended to mean a butane wherein the hydrogens are partially substituted by chlorines and fluorines. A halobutane starting material in this disclosure is selected from the group consisting of $CF_2HCHClCH_2CCl_2H$, $CF_2HCHClCH_2CCl_3$, $CF_3CHClCH_2CCl_2H$, $CF_3CHClCH_2CCl_3$, $CF_3CHClCHClCCl_2H$, $CF_3CHClCHClCCl_3$, $CF_3CCl_2CH_2CCl_2H$, $CF_3CCl_2CH_2CCl_3$, $CF_3CCl_2CHClCCl_2H$, $CF_3CCl_2CHClCCl_3$, $CF_3CClFCHClCCl_2H$, $CF_3CClFCHClCCl_3$, $CF_3CClFCH_2CCl_2H$, $CF_3CClFCH_2CCl_3$, $CF_3CClFCHFCCl_2H$, $CF_3CClFCHFCCl_3$, $CF_3CClHCHFCCl_2H$ and $CF_3CClHCHFCCl_3$.

In one embodiment of this invention, the halobutane starting material is $CF_2HCHClCH_2CCl_2H$ and the resulting internal fluorobutene product is $CF_2HCH=CHCF_2H$.

In another embodiment of this invention, the halobutane starting material is $CF_2HCHClCH_2CCl_3$, $CF_3CHClCH_2CCl_2H$, or mixtures thereof, and the resulting internal fluorobutene product is $CF_3CH=CHCF_2H$.

In another embodiment of this invention, the halobutane starting material is $CF_3CHClCH_2CCl_3$ and the resulting internal fluorobutene product is $CF_3CH=CHCF_3$.

In another embodiment of this invention, the halobutane starting material is $CF_3CHClCHClCCl_2H$ and the resulting internal fluorobutene product is $CF_3CF=CHCF_2H$, $CF_3CH=CFCF_2H$, or mixtures thereof.

In another embodiment of this invention, the halobutane starting material is selected from the group consisting of $CF_3CHClCHClCCl_3$, $CF_3CCl_2CH_2CCl_3$, $CF_3CClHCHFCCl_3$ and $CF_3CClFCH_2CCl_3$, and the resulting internal fluorobutene product is $CF_3CF=CHCF_3$.

In another embodiment of this invention, the halobutane starting material is $CF_3CCl_2CH_2CCl_2H$, $CF_3CClFCH_2CCl_2H$, or mixtures thereof, and the resulting internal fluorobutene product is $CF_3CF=CHCF_2H$.

In another embodiment of this invention, the halobutane starting material is selected from the group consisting of $CF_3CCl_2CHClCCl_2H$, $CF_3CClFCHClCCl_2H$ and $CF_3CClFCHFCCl_2H$, and the resulting internal fluorobutene product is $CF_3CF=CFCF_2H$.

In another embodiment of this invention, the halobutane starting material is selected from the group consisting of $CF_3CCl_2CHClCCl_3$, $CF_3CClFCHClCCl_3$, $CF_3CClFCHFCCl_3$, and the resulting internal fluorobutene product is $CF_3CF=CFCF_3$.

In another embodiment of this invention, the halobutane starting material is $CF_3CClHCHFCCl_2H$ and the resulting internal fluorobutene product is $CF_3CH=CFCF_2H$.

The term "halopentane" is intended to mean a pentane wherein the hydrogens are partially substituted by fluorines, chlorine(s) and/or bromine(s). A halopentane starting material in this disclosure can be represented by the formula $CF_2HCHXCH_2CX_2CX_3$, $CF_3CHXCH_2CX_2CX_3$, $CF_3CHXCHXCX_2CX_3$, $CF_3CX_2CH_2CX_2CX_3$, $CF_3CX_2CHXCX_2CX_3$ or $CF_3CHXCHFCX_2CX_3$, wherein each X is independently selected from the group consisting of F, Cl and Br, provided that not all X are fluorines.

Examples of halopentane starting materials of the formula $CF_2HCHXCH_2CX_2CX_3$ include $CF_2HCHClCH_2CCl_2CCl_3$, $CF_2HCHClCH_2CClFCCl_3$, $CF_2HCHClCH_2CCl_2CF_3$, $CF_2HCHClCH_2CClFCF_3$, $CF_2HCHClCH_2CCl_2CClF_2$, $CF_2HCHBrCH_2CCl_2CCl_3$, $CF_2HCHBrCH_2CClFCCl_3$, $CF_2HCHBrCH_2CClBrCF_3$, $CF_2HCHBrCH_2CBr_2CF_3$, $CF_2HCHBrCH_2CBr_2CCl_3$ and $CF_2HCHBrCH_2CCl_2CClF_2$.

Examples of halopentane starting materials of the formula $CF_3CHXCH_2CX_2CX_3$ include $CF_3CHClCH_2CCl_2CCl_3$, $CF_3CHClCH_2CClFCCl_3$, $CF_3CHClCH_2CCl_2CF_3$, $CF_3CHClCH_2CClFCF_3$, $CF_3CHClCH_2CCl_2CClF_2$, $CF_3CHBrCH_2CCl_2CCl_3$, $CF_3CHBrCH_2CClFCCl_3$, $CF_3CHBrCH_2CClBrCF_3$, $CF_3CHBrCH_2CBr_2CF_3$, $CF_3CHBrCH_2CBr_2CCl_3$ and $CF_3CHBrCH_2CCl_2CClF_2$.

Examples of halopentane starting materials of the formula $CF_3CHXCHXCX_2CX_3$ include $CF_3CHClCHClCCl_2CCl_3$, $CF_3CHClCHClCClFCCl_3$, $CF_3CHClCHClCCl_2CF_3$, $CF_3CHClCHClCClFCF_3$, $CF_3CHClCHClCCl_2CClF_2$, $CF_3CHBrCHClCCl_2CCl_3$, $CF_3CHBrCHClCClFCCl_3$, $CF_3CHBrCHClCClBrCF_3$, $CF_3CHBrCHClCBr_2CF_3$, $CF_3CHBrCHClCBr_2CCl_3$ and $CF_3CHBrCHClCCl_2CClF_2$.

Examples of halopentane starting materials of the formula $CF_3CX_2CH_2CX_2CX_3$ include $CF_3CCl_2CH_2CCl_2CCl_3$, $CF_3CCl_2CH_2CClFCCl_3$, $CF_3CCl_2CH_2CCl_2CF_3$, $CF_3CCl_2CH_2CClFCF_3$, $CF_3CCl_2CH_2CCl_2CClF_2$, $CF_3CCl_2CH_2CCl_2CCl_3$, $CF_3CClBrCH_2CClFCCl_3$, $CF_3CClBrCH_2CClBrCF_3$, $CF_3CClBrCH_2CBr_2CF_3$, $CF_3CClBrCH_2CBr_2CCl_3$, $CF_3CClBrCH_2CCl_2CClF_2$, $CF_3CFClCH_2CCl_2CCl_3$, $CF_3CFClCH_2CClFCCl_3$, $CF_3CFClCH_2CCl_2CF_3$, $CF_3CFClCH_2CClFCF_3$, $CF_3CFClCH_2CCl_2CClF_2$, $CF_3CFBrCH_2CCl_2CCl_3$, $CF_3CFBrCH_2CClFCCl_3$, $CF_3CFBrCH_2CClBrCF_3$, $CF_3CFBrCH_2CBr_2CF_3$, $CF_3CFBrCH_2CBr_2CCl_3$ and $CF_3CFBrCH_2CCl_2CClF_2$.

Examples of halopentane starting materials of the formula $CF_3CX_2CHXCX_2CX_3$ include $CF_3CCl_2CHClCCl_2CCl_3$, $CF_3CCl_2CHClCClFCCl_3$, $CF_3CCl_2CHClCCl_2CF_3$, $CF_3CCl_2CHClCClFCF_3$, $CF_3CCl_2CHClCCl_2CClF_2$, $CF_3CClBrCHClCCl_2CCl_3$, $CF_3CClBrCHClCClFCCl_3$, $CF_3CClBrCHClCClBrCF_3$, $CF_3CClBrCHClCBr_2CF_3$, $CF_3CClBrCHClCBr_2CCl_3$, $CF_3CClBrCHClCCl_2CClF_2$, $CF_3CFClCHFCCl_2CCl_3$, $CF_3CFClCHFCClFCCl_3$, $CF_3CFClCHFCCl_2CF_3$, $CF_3CFClCHFCClFCF_3$, $CF_3CFClCHFCCl_2CClF_2$, $CF_3CFBrCHFCCl_2CCl_3$, $CF_3CFBrCHFCClFCCl_3$, $CF_3CFBrCHFCClBrCF_3$, $CF_3CFBrCHFCBr_2CF_3$, $CF_3CFBrCHFCBr_2CCl_3$ and $CF_3CFBrCHFCCl_2CClF_2$.

Examples of halopentane starting materials of the formula $CF_3CHXCHFCX_2CX_3$ include $CF_3CHClCHFCCl_2CCl_3$, $CF_3CHClCHFCClFCCl_3$, $CF_3CHClCHFCCl_2CF_3$, $CF_3CHClCHFCClFCF_3$, $CF_3CHClCHFCClFCF_3$, $CF_3CHClCHFCCl_2CClF_2$, $CF_3CHBrCHFCCl_2CCl_3$, $CF_3CHBrCHFCClFCCl_3$, $CF_3CHBrCHFCClBrCF_3$, $CF_3CHBrCHFCBr_2CF_3$, $CF_3CHBrCHFCBr_2CCl_3$, $CF_3CHBrCHFCCl_2CClF_2$.

In one embodiment of this invention, the halopentane starting material is $CF_2HCHXCH_2CX_2CX_3$ and the resulting internal fluoropentene product is $CF_2HCH=CHCF_2CF_3$.

In another embodiment of this invention, the halopentane starting material is $CF_3CHXCH_2CX_2CX_3$ and the resulting internal fluoropentene product is $CF_3CH=CHCF_2CF_3$.

In another embodiment of this invention, the halopentane starting material is $CF_3CHXCHXCX_2CX_3$ and the resulting internal fluoropentene product is $CF_3CH=CFCF_2CF_3$, $CF_3CF=CHCF_2CF_3$, or mixtures thereof.

In another embodiment of this invention, the halopentane starting material is $CF_3CX_2CH_2CX_2CX_3$ and the resulting internal fluoropentene product is $CF_3CF=CHCF_2CF_3$.

In another embodiment of this invention, the halopentane starting material is $CF_3CX_2CHXCX_2CX_3$ and the resulting internal fluoropentene product is $CF_3CF=CFCF_2CF_3$.

In another embodiment of this invention, the halopentane starting material is $CF_3CHXCHFCX_2CX_3$ and the resulting internal fluoropentene product is $CF_3CH=CFCF_2CF_3$.

Halobutane starting materials may be prepared by the processes known in the art or disclosed in Russian Patent Application Numbers 2010147009, 2010147008 and 20100147002 [FL1564, FL1565 and FL1388] filed concurrently herewith, and hereby incorporated by reference in their entirety.

Halopentane starting materials may be prepared by the processes known in the art or disclosed in Russian Patent Application Numbers 2010147009, 2010147008 and 20100147002 [FL1564, FL1565 and FL1388] filed concurrently herewith, and hereby incorporated by reference in their entirety.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

The processes of this disclosure use a molar ratio of HF to the halobutane or halopentane starting material that is at least stoichiometric. The stoichiometric amount is the total number of Cl and/or Br substituents on the halobutane or halopentane starting materials minus one. For example, the stoichiometric ratio of HF to $CF_3CHClCH_2CCl_2CF_3$ is 2:1. As another example, the stoichiometric ratio of HF to $CF_2HCHBrCH_2CCl_2CCl_3$ is 5:1.

The molar ratio of HF to the halobutane or halopentane starting material is typically from about the stoichiometric amount to about 50:1. In some embodiments of this invention, the molar ratio of HF to the halobutane or halopentane starting material is from about twice the stoichiometric amount to about 30:1. In some embodiments of this invention, the molar ratio of HF to the halobutane or halopentane starting material is from about twice the stoichiometric amount to about 20:1.

The term "a chromium oxyfluoride catalyst" is intended to mean a chromium oxyfluoride represented by formula $Cr_2O_xF_y$, wherein $x+y/2=3$.

The term "amorphous" is intended to mean that there is no substantial peak in a X-ray diffraction pattern of the subject solid.

The chromium oxyfluoride catalysts can be made by treating $Cr_2O_3$ with HF, $CCl_3F$, $COF_2$ or hydrofluorocarbons. In one embodiment of this invention, a chromium oxyfluoride catalyst is made by treating dry $Cr_2O_3$ with a fluorination agent such as $CCl_3F$ or HF. This treatment can be accomplished by placing the dry $Cr_2O_3$ in a suitable container (which can be the reactor to be used to perform the subsequent catalytical reaction) and thereafter passing HF over the dry $Cr_2O_3$ for a suitable period of time (e.g., about 15 to about 800 minutes) at a suitable temperature (e.g., about 200° C. to about 450° C.), such as what described in Example 1.

In another embodiment of this invention, a chromium oxyfluoride catalyst is made by treating $Cr_2O_3$ with a hydrofluorocarbon at an elevated temperature.

In another embodiment of this invention, a chromium oxyfluoride catalyst is made in situ. For example, the starting material $CF_3CHClCHFCClFCCl_3$, $CF_3CHClCHFCCl_2CF_3$ or $CF_3CHClCHFCClFCF_3$ can be employed in the formation of a chromium oxyfluoride catalyst by heating it together with $Cr_2O_3$ in the reactor.

$Cr_2O_3$ is commercially available from BASF Catalysts LLC, 25 Middlesex Essex Tumpike, Iselin, N.J. 08830-0770.

$Cr_2O_3$ can also be prepared by reducing chromium (VI) oxide in water with a suitable reducing agent, such as ethanol, as disclosed in U.S. Pat. No. 3,258,500, which is incorporated herein by reference. Of note is the so-called gel-type activated $Cr_2O_3$ obtained by reducing chromium trioxide ($CrO_3$) and dehydrating the reduced product in the manner disclosed by Ruthruff in "Inorganic Synthesis", Vol. II, pp. 190-193, published in 1946 by McGraw-Hill Book Co., New York, and by Turkevich and Ruthruff in U.S. Pat. No. 2,271,356, both of which are incorporated herein by reference. In one embodiment of this invention, $Cr_2O_3$ is prepared by dissolving chromium trioxide in water, gradually adding ethanol or other suitable reducing agent to the solution and heating under reflux conditions until the $Cr_2O_3$ gel precipitates, separating the gel from the reaction mixture, drying it, and then dehydrating and activating the product by heating it at a temperature of from about 400° C. to about 600° C. in an inert atmosphere until the water is removed and an anhydrous product is obtained.

$Cr_2O_3$ can also be prepared by pyrolysis of ammonium dichromate (($NH_4)_2Cr_2O_7$) as disclosed in U.S. Pat. No. 5,036,036, which is incorporated herein by reference. Of note is $Cr_2O_3$ prepared by pyrolysing ammonium dichromate and treating (e.g., washing with deionized water) the resulting $Cr_2O_3$ to reduce the alkali metal content to 100 ppm or less. Also of note is $Cr_2O_3$ prepared by first treating ammonium dichromate containing 60-2000 ppm alkali metal to reduce its alkali metal content to less than 60 ppm and then pyrolysing the resulting ammonium dichromate with reduced alkali metal content to form $Cr_2O_3$ containing 100 ppm or less of alkali metal content.

$Cr_2O_3$ can also be prepared by the reaction of chromium (VI) oxide with a reducing solvent, such as methanol, as disclosed in U.S. Pat. No. 4,828,818, which is incorporated herein by reference.

The amount of potassium and other alkali metals in $Cr_2O_3$ can be reduced by a water washing step as disclosed in U.S. Pat. No. 5,036,036.

In one embodiment of this invention, the chromium oxyfluoride catalyst has surface area of from about 10 m$^2$/g to about 800 m$^2$/g.

In another embodiment of this invention, the chromium oxyfluoride catalyst has surface area of from about 20 m$^2$/g to about 400 m$^2$/g.

In another embodiment of this invention, the chromium oxyfluoride catalyst has surface area of from about 40 m$^2$/g to about 300 m$^2$/g.

In one embodiment of this invention, the chromium oxyfluoride catalyst contains an alkali metal content of about 2000 ppm or less.

In another embodiment of this invention, the chromium oxyfluoride catalyst contains an alkali metal content of about 300 ppm or less.

In another embodiment of this invention, the chromium oxyfluoride catalyst contains an alkali metal content of about 100 ppm or less.

In one embodiment of this invention, the chromium oxyfluoride catalyst is amorphous.

In another embodiment of this invention, the chromium oxyfluoride catalyst is prepared from crystalline α-$Cr_2O_3$.

The form of the catalyst is not critical and may be used as pellets, powders or granules.

The temperature employed in the reaction zone for the catalytical reactions of this disclosure typically ranges from about 200° C. to about 500° C. In some embodiments of this invention, the temperature employed in the reaction zone for the catalytical reactions ranges from about 300° C. to about 400° C.

The contacting time of the halobutane or halopentane starting material with HF in the reaction zone in the presence of the chromium oxyfluoride catalyst is not critical and typically ranges from about 0.1 second to about 1000 seconds. In some embodiments of this invention, the contacting time ranges from about 5 seconds to about 100 seconds.

The pressure in the reaction zone for the catalytical reactions of this disclosure can be subatmospheric, atmospheric or superatmospheric. In some embodiments of this invention, the pressure in the reaction zone is near atmospheric.

Optionally, the catalytical reactions of this disclosure can be conducted in the presence of oxygen. In some embodiments of this invention, the catalytical reactions are conducted in the presence of air. In some embodiments of this invention, air is co-fed with the starting materials (halobutane, halopentane, HF, halobutane/HF mixtures or halopentane/HF mixtures) into the reaction zone.

Optionally, the catalytical reactions of this disclosure can be conducted in the presence of inert gases such as nitrogen, helium, argon, or their mixtures thereof. In some embodiments of this invention, the inert gas is co-fed with the starting materials (halobutane, halopentane, HF, halobutane/HF mixtures or halopentane/HF mixtures) into the reaction zone. In some embodiments of this invention, the inert gas is nitrogen.

In some embodiments of this invention, the desired internal fluorobutene or internal fluoropentene product may be recovered from the product mixture by fractional distillation.

The reactors, distillation columns, and their associated feed lines, effluent lines, and associated units used in applying the processes of embodiments of this invention should be constructed of materials resistant to corrosion. Typical materials of construction include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

Many aspects and embodiments have been described above and are merely exemplary and not limiting. After reading this specification, skilled artisans appreciate that other aspects and embodiments are possible without departing from the scope of the invention.

EXAMPLES

The concepts described herein will be further described in the following examples, which do not limit the scope of the invention described in the claims.

Example 1

Example 1 demonstrates a method for preparing the chromium oxyfluoride catalyst.

6 cc (cubic centimeter) (7.3 gm) of $Cr_2O_3$ gel pellets prepared according to the process described in U.S. Pat. No. 3,258,500, Example 1(A), were crushed and sieved to 12/20 mesh, and filled into an Inconel™ tube (⅝ inch OD) to form a catalyst bed. The $Cr_2O_3$ was heated to 400° C. under a purge of nitrogen (38 sccm (standard cubic centimeters per minute)) for 120 minutes and then at 300° C. for 80 minutes while continuing the nitrogen purge. Then the nitrogen flow was reduced to 28 sccm and HF was fed into the tube at 9 sccm for 45 minutes. While maintaining HF and nitrogen flows, the temperature was raised to 325° C. for 80 minutes, to 350° C. for 80 minutes, 375° C. for 200 minutes, 400° C. for 40 minutes, and 425° C. for 55 minutes. While keeping the temperature at 400° C., the flow of nitrogen was lowered to 19 sccm and the flow of HF was raised to 15 sccm for 25 minutes. The flow of nitrogen was then lowered to 11 sccm and the flow of HF was raised to 21 sccm for 30 minutes. The flow of nitrogen was then lowered to 4 sccm and the flow of HF was raised to 27 sccm for 30 minutes. The flow of nitrogen was then discontinued and the flow of HF was raised to 30 sccm for 160 minutes.

Example 2

Example 2 demonstrates that $CF_3CHClCH_2CCl_2CF_3$ can react with HF in the presence of a chromium oxyfluoride catalyst to produce $CF_3CH=CHCF_2CF_3$.

The chromium oxyfluoride catalyst prepared in Example 1 was used here. After the HF treatment in Example 1, the tube temperature was lowered to 348° C. and stabilized. $CF_3CHClCH_2CCl_2CF_3$ was fed into a vaporizer at 0.55 ml/hour and was vaporized at 140° C. Nitrogen was flowed through the vaporizer at 3 sccm and carried the vaporized $CF_3CHClCH_2CCl_2CF_3$ to the tube while HF was flowed through the tube at 8.3 sccm. Part of the reactor tube effluent was analyzed by on line GC/MS. The analytical result after three hours of continuous operation was shown in Table 1 below.

TABLE 1

| Component | Mole percent |
|---|---|
| $CCl_2FCF_3$ | 0.9% |
| $CF_3CH=CFCF_2CF_3$ | 3.2% |
| E-$CF_3CH=CHCF_2CF_3$ | 42.6% |
| $C_5HClF_8$ isomers | 18.2% |
| $C_5H_2ClF_7$ isomer 1 | 3.5% |
| $C_5H_2ClF_7$ isomer 2 | 1.1% |
| $C_5H_2ClF_7$ isomer 3 | 1.1% |
| $CF_3CH=CHCHClCF_3$ | 6.2% |

TABLE 1-continued

| Component | Mole percent |
|---|---|
| $CF_3CH=CHCCl_2CF_3$ | 16.2% |
| Unknowns | 7.0% |

Example 3

Example 3 also demonstrates that $CF_3CHClCH_2CCl_2CF_3$ can react with HF in the presence of a chromium oxyfluoride catalyst to produce $CF_3CH=CHCF_2CF_3$.

Another batch of chromium oxyfluoride catalyst was prepared according to Example 1 by using 7.2 gm of $Cr_2O_3$ gel pellets. The tube temperature was lowered to 323° C. and stabilized. $CF_3CHClCH_2CCl_2CF_3$ was fed into a vaporizer at 0.55 ml/hour and was vaporized at 140° C. Nitrogen was flowed through the vaporizer at 3 sccm and carried the vaporized $CF_3CHClCH_2CCl_2CF_3$ to the tube while HF was flowed through the tube at 8.3 sccm. Part of the reactor tube effluent was analyzed by on line GC/MS. The analytical result after one hour of continuous operation was shown in Table 2 below.

TABLE 2

| Component | Mole percent |
|---|---|
| $CCl_2FCF_3$ | 0.3% |
| $CF_3CH=CFCF_2CF_3$ | 1.3% |
| E-$CF_3CH=CHCF_2CF_3$ | 52.1% |
| $C_5HClF_8$ isomers | 17.9% |
| $C_5H_2ClF_7$ isomer 1 | 2.5% |
| $C_5H_2ClF_7$ isomer 2 | 0.8% |
| $C_5H_2ClF_7$ isomer 3 | 0.7% |
| $CF_3CH=CHCHClCF_3$ | 0.1% |
| $CF_3CH=CHCCl_2CF_3$ | 19.0% |
| Unknowns | 5.3% |

Example 4

Example 4 demonstrates that $CF_3CHClCH_2CHCl_2$ can react with HF in the presence of a chromium oxyfluoride catalyst to produce $CF_3CH=CHCHF_2$.

Another batch of chromium oxyfluoride catalyst was prepared according to Example 1 by using 7.4 gm of $Cr_2O_3$ gel pellets. The tube temperature was lowered to 323° C. and stabilized. $CF_3CHClCH_2CHCl_2$ was fed into a vaporizer at 0.60 ml/hour and was vaporized at 150° C. Nitrogen was flowed through the vaporizer at 2 sccm and carried the vaporized $CF_3CHClCH_2CHCl_2$ to the tube while HF was flowed through the tube at 20.4 sccm. Part of the reactor tube effluent was analyzed by on line GC/MS. The analytical result after six hours of continuous operation was shown in Table 3 below.

TABLE 3

| Component | Mole percent |
|---|---|
| E-$CF_3CH=CHCF_3$ | 6.5% |
| E-$CF_3CH=CHCHF_2$ | 83.2% |
| E-$CF_3CH=CHCF_3$ | 0.1% |
| $CF_3CHClCH_2CF_3$ | 0.3% |
| $CF_3CHClCH_2CHF_2$ | 1.8% |
| Unknowns | 8.1% |

Example 5

Example 5 demonstrates that $CF_3CF_2CHClCH_2CCl_3$ can react with HF in the presence of a chromium oxyfluoride catalyst to produce $CF_3CH=CHCF_2CF_3$.

Another batch of chromium oxyfluoride catalyst was prepared according to Example 1 by using 7.32 gm of $Cr_2O_3$ gel pellets. The tube temperature was lowered to 273° C. and stabilized. $CF_3CF_2CHClCH_2CCl_3$ was fed into a vaporizer at 0.82 ml/hour and was vaporized at 165° C. Nitrogen was flowed through the vaporizer at 4 sccm and carried the vaporized $CF_3CF_2CHClCH_2CCl_3$ to the tube while HF was flowed through the tube at 11.8 sccm. Part of the reactor tube effluent was analyzed by on line GC/MS. The analytical result after six hours of continuous operation was shown in Table 4 below.

TABLE 4

| Component | Mole percent |
|---|---|
| E-$CF_3CH=CHCF_2CF_3$ | 71.0% |
| $CF_3CF=CHCF_2CF_3$ | 0.7% |
| E-$CF_3CH=CHCF_2CF_3$ | 0.2% |
| $CF_3CH=CClCF_3$ | 0.2% |
| $CCl_2FCClF_2$ | 0.5% |
| $CF_3CCl=CHCF_2CF_3$ | 9.0% |
| $CF_2ClCH=CHCF_2CF_3$ | 3.7% |
| $CFCl_2CH=CHCF_2CF_3$ | 7.5% |
| Unknowns | 7.2% |

Example 6

Example 6 demonstrates that $CF_3CFClCH_2CCl_3$ can react with HF in the presence of a chromium oxyfluoride catalyst to produce $CF_3CH=CFCF_3$.

The same batch of catalyst as in the Example 5 was used here. The tube temperature was raised to 302° C. and stabilized. $CF_3CFClCH_2CCl_3$ was fed into a vaporizer at 0.92 ml/hour and was vaporized at 160° C. Nitrogen was flowed through the vaporizer at 3.7 sccm and carried the vaporized $CF_3CFClCH_2CCl_3$ to the tube while HF was flowed through the tube at 10.0 sccm. Part of the reactor tube effluent was analyzed by on line GC/MS. The analytical result after fourteen hours of continuous operation was shown in Table 5 below.

TABLE 5

| Component | Mole percent |
|---|---|
| Z—$CF_3CH=CFCF_3$ | 14.8% |
| $CF_3CH_2CF_2CF_3$ | 11.5% |
| E-$CF_3CH=CClCF_3$ | 70.4% |
| Z—$CF_3CH=CClCF_3$ | 2.8% |
| Unknowns | 0.5% |

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A vapor phase process for making internal fluorobutenes comprising contacting a halobutane starting material selected from the group consisting of $CF_2HCHClCH_2CCl_2H$, $CF_2HCHClCH_2CCl_3$, $CF_3CHClCH_2CCl_2H$, $CF_3CHClCH_2CCl_3$, $CF_3CHClCHClCCl_2H$, $CF_3CHClCHClCCl_3$, $CF_3CCl_2CH_2CCl_2H$, $CF_3CCl_2CH_2CCl_3$, $CF_3CCl_2CHClCCl_2H$, $CF_3CCl_2CHClCCl_3$, $CF_3CClFCHClCCl_2H$, $CF_3CClFCHClCCl_3$, $CF_3CClFCH_2CCl_2H$, $CF_3CClFCHFCCl_2H$, $CF_3CClFCHFCCl_3$, $CF_3CClHCHFCCl_2H$ and $CF_3CClHCHFCCl_3$, with HF in a reaction zone in the presence of a catalyst consisting of chromium oxyfluoride to produce a product mixture comprising at least one fully fluorinated internal fluorobutene, wherein the at least one internal fluorobutene is present in the product mixture at an amount of greater than 15 mole percent.

2. The vapor phase process of claim 1 wherein said halobutane starting material is $CF_2HCHClCH_2CCl_2H$ and said at least one fully fluorinated internal fluorobutene is $CF_2HCH=CHCF_2H$.

3. The vapor phase process of claim 1 wherein said halobutane starting material is $CF_3CHClCH_2CCl_3$ and said at least one fully fluorinated internal fluorobutene is $CF_3CH=CHCF_3$.

4. The vapor phase process of claim 1 wherein said halobutane starting material is $CF_3CHClCHClCCl_2H$ and said at least one fully fluorinated internal fluorobutene is $CF_3CF=CHCF_2H$, $CF_3CH=CFCF_2H$, or mixtures thereof.

5. The vapor phase process of claim 1 wherein said halobutane starting material is selected from the group consisting of $CF_3CHClCHClCCl_3$, $CF_3CCl_2CH_2CCl_3$, and $CF_3CClHCHFCCl_3$, and said at least one fully fluorinated internal fluorobutene is $CF_3CF=CHCF_3$.

6. The vapor phase process of claim 1 wherein said halobutane starting material is $CF_3CCl_2CH_2CCl_2H$, $CF_3CClFCH_2CCl_2H$, or mixtures thereof, and said at least one fully fluorinated internal fluorobutene is $CF_3CF=CHCF_2H$.

7. The vapor phase process of claim 1 wherein said halobutane starting material is selected from the group consisting of $CF_3CCl_2CHClCCl_2H$, $CF_3CClFCHClCCl_2H$ and $CF_3CClFCHFCCl_2H$, and said at least one fully fluorinated internal fluorobutene is $CF_3CF=CFCF_2H$.

8. The vapor phase process of claim 1 wherein said halobutane starting material is selected from the group consisting of $CF_3CCl_2CHClCCl_3$, $CF_3CClFCHClCCl_3$, $CF_3CClFCHFCCl_3$, and said at least one fully fluorinated internal fluorobutene is $CF_3CF=CFCF_3$.

9. The vapor phase process of claim 1 wherein said halobutane starting material is $CF_3CClHCHFCCl_2H$ and said at least one fully fluorinated internal fluorobutene is $CF_3CH=CFCF_2H$.

10. A vapor phase process for making internal fluoropentenes comprising contacting a halopentane starting material selected from the group consisting of $CF_2HCHXCH_2CX_2CX_3$, $CF_3CHXCH_2CX_2CX_3$, $CF_3CHXCHXCX_2CX_3$, $CF_3CX_2CH_2CX_2CX_3$, $CF_3CX_2CHXCX_2CX_3$ and $CF_3CHXCHFCX_2CX_3$, with HF in a reaction zone in the presence of a catalyst consisting of chromium oxyfluoride to produce a product mixture comprising at least one fully fluorinated internal fluoropentene, wherein each X is independently selected from the group consisting of F, Cl and Br, provided that not all X are fluorines, and wherein the at least one fully fluorinated internal fluorobutene is present in the product mixture at an amount of greater than 15 mole percent.

11. The vapor phase process of claim 10 wherein said halopentane starting material is $CF_2HCHXCH_2CX_2CX_3$ and said at least one fully fluorinated internal fluoropentene is $CF_2HCH=CHCF_2CF_3$.

12. The vapor phase process of claim 11 wherein said halopentane starting material is selected from the group consisting of $CF_2HCHClCH_2CCl_2CCl_3$, $CF_2HCHClCH_2CClFCCl_3$, $CF_2HCHClCH_2CCl_2CF_3$, $CF_2HCHClCH_2CClFCF_3$, $CF_2HCHClCH_2CCl_2CClF_2$, $CF_2HCHBrCH_2CCl_2CCl_3$, $CF_2HCHBrCH_2CClFCCl_3$, $CF_2HCHBrCH_2CClBrCF_3$, $CF_2HCHBrCH_2CBr_2CF_3$, $CF_2HCHBrCH_2CBr_2CCl_3$ and $CF_2HCHBrCH_2CCl_2CClF_2$.

13. The vapor phase process of claim 10 wherein said halopentane starting material is $CF_3CHXCH_2CX_2CX_3$ and said at least one fully fluorinated internal fluoropentene is $CF_3CH=CHCF_2CF_3$.

14. The vapor phase process of claim 13 wherein said halopentane starting material is selected from the group consisting of $CF_3CHClCH_2CCl_2CCl_3$, $CF_3CHClCH_2CClFCCl_3$, $CF_3CHClCH_2CCl_2CF_3$, $CF_3CHClCH_2CClFCF_3$, $CF_3CHClCH_2CCl_2CClF_2$, $CF_3CHBrCH_2CCl_2CCl_3$, $CF_3CHBrCH_2CClFCCl_3$, $CF_3CHBrCH_2CClBrCF_3$, $CF_3CHBrCH_2CBr_2CF_3$, $CF_3CHBrCH_2CBr_2CCl_3$ and $CF_3CHBrCH_2CCl_2CClF_2$.

15. The vapor phase process of claim 10 wherein said halopentane starting material is $CF_3CHXCHXCX_2CX_3$ and said at least one fully fluorinated internal fluoropentene is $CF_3CH=CFCF_2CF_3$, $CF_3CF=CHCF_2CF_3$, or mixtures thereof.

16. The vapor phase process of claim 15 wherein said halopentane starting material is selected from the group consisting of $CF_3CHClCHClCCl_2CCl_3$, $CF_3CHClCHClCClFCCl_3$, $CF_3CHClCHClCCl_2CF_3$, $CF_3CHClCHClCClFCF_3$, $CF_3CHClCHClCCl_2CClF_2$, $CF_3CHBrCHClCCl_2CCl_3$, $CF_3CHBrCHClCClFCCl_3$, $CF_3CHBrCHClCClBrCF_3$, $CF_3CHBrCHClCBr_2CF_3$, $CF_3CHBrCHClCBr_2CCl_3$ and $CF_3CHBrCHClCl2CClF_2$.

17. The vapor phase process of claim 10 wherein said halopentane starting material is $CF_3CX_2CH_2CX_2CX_3$ and said at least one fully fluorinated internal fluoropentene is $CF_3CF=CHCF_2CF_3$.

18. The vapor phase process of claim 17 wherein said halopentane starting material is selected from the group consisting of $CF_3CCl_2CH_2CCl_2CCl_3$, $CF_3CCl_2CH_2CClFCCl_3$, $CF_3CCl_2CH_2CCl_2CF_3$, $CF_3CCl_2CH_2CClFCF_3$, $CF_3CCl_2CH_2CCl_2CClF_2$, $CF_3CCl_2CH_2CCl_2CCl_3$, $CF_3CClBrCH_2CClFCCl_3$, $CF_3CClBrCH_2CClBrCF_3$, $CF_3CClBrCH_2CBr_2CF_3$, $CF_3CClBrCH_2CBr_2CCl_3$, $CF_3CClBrCH_2CCl_2CClF_2$, $CF_3CFClCH_2CCl_2CCl_3$, $CF_3CFClCH_2CClFCCl_3$, $CF_3CFClCH_2CCl_2CF_3$, $CF_3CFClCH_2CClFCF_3$, $CF_3CFClCH_2CCl_2CClF_2$, $CF_3CFBrCH_2CCl_2CCl_3$, $CF_3CFBrCH_2CClFCCl_3$, $CF_3CFBrCH_2CClBrCF_3$, $CF_3CFBrCH_2CBr_2CF_3$, $CF_3CFBrCH_2CBr_2CCl_3$ and $CF_3CFBrCH_2CCl_2CClF_2$.

19. The vapor phase process of claim 10 wherein said halopentane starting material is $CF_3CX_2CHXCX_2CX_3$ and said at least one fully fluorinated internal fluoropentene is $CF_3CF=CFCF_2CF_3$.

20. The vapor phase process of claim 10 wherein said halopentane starting material is $CF_3CHXCHFCX_2CX_3$ and said at least one fully fluorinated internal fluoropentene is $CF_3CH=CFCF_2CF_3$.

* * * * *